United States Patent [19]

Saydek et al.

[11] Patent Number: 4,863,696
[45] Date of Patent: Sep. 5, 1989

[54] APPARATUS FOR THE PERCUTANEOUS ABSORPTION OF FLUIDS

[75] Inventors: Michael E. Saydek, Somerville, N.J.; Gordon Flynn, Ann Arbor, Mich.; Karlis Vizulis, Saline, Mich.; Charles Von Reis, Ann Arbor, Mich.

[73] Assignee: Crown Glass Company, Inc., Somerville, N.J.

[21] Appl. No.: 244,544

[22] Filed: Sep. 12, 1988

Related U.S. Application Data

[63] Continuation of Ser. No. 80,670, Aug. 3, 1987, abandoned.

[51] Int. Cl.⁴ .............................................. G01N 33/48
[52] U.S. Cl. .................................... 422/101; 422/83; 436/178; 73/38; 73/64.3; 210/232; 210/321.6; 210/321.84; 210/335; 210/339; 210/433.1; 210/445; 210/451
[58] Field of Search ................... 73/38, 64.3; 210/232, 210/321.6, 321.84, 335, 339, 433.1, 445, 451; 422/83, 101; 436/178

[56] References Cited

U.S. PATENT DOCUMENTS

| | | | |
|---|---|---|---|
| 3,565,256 | 2/1971 | Loeffler | 210/445 X |
| 3,888,576 | 6/1975 | Bolk | 210/445 X |
| 3,932,153 | 1/1976 | Byrns | 210/445 X |
| 4,428,907 | 1/1984 | Heijenga et al. | 422/83 X |
| 4,632,807 | 12/1986 | Marsoner | 422/83 X |
| 4,643,878 | 2/1987 | Seiter et al. | 422/101 |
| 4,678,576 | 7/1987 | Leoncavallo | 210/445 X |
| 4,767,602 | 8/1988 | Johnson | 422/101 |
| 4,769,333 | 9/1988 | Dole et al. | 422/101 X |

*Primary Examiner*—Barry S. Richman
*Assistant Examiner*—Lynn M. Kummert
*Attorney, Agent, or Firm*—Kenneth A. Koch

[57] ABSTRACT

An orifice assembly for use in connection with diffusion cells for the percutaneous absorption of fluids which is composed of a pair of resiliant and mating members having structure for securely retaining a flexible membrane therebetween in a predetermined and fluid tight relationship with each other and the diffusion cells.

1 Claim, 1 Drawing Sheet

APPARATUS FOR THE PERCUTANEOUS ABSORPTION OF FLUIDS

RELATED APPLICATIONS

This is a continuation of co-pending application Ser. No. 080,670 filed on Aug. 3, 1987, now abandoned.

This application is related to pending application Ser. No. 06/817,346 filed Jan. 9, 1986, now abandoned.

BACKGROUND OF THE INVENTION

The invention relates to the percutaneous absorption of solutions containing pharmaceutical compounds, cosmetics and toxic substances through permeable membranes such as human skin. In particular, the invention pertains to devices used to facilitate percutaneous absorption and improvements thereon.

Percutaneous absorption has recently become a standard technique in the drug industry for studying the flow of various active ingredient compounds into the human body through the skin. The technique most commonly used is known as the infinite dose technique in which human skin is mounted as a barrier between two well stirred fluid filled chambers. The compound under study is added to the solution on one side (donor) of the membrane and absorption assessed by serially sampling and assaying its concentration in the bathing solution (receptor) on the other side of the membrane. The apparatus used in the infinite dose technique is constructed of glass for easy visibility of the process by the researcher and to avoid the leaching of foreign materials into either the donor or receptor solutions.

A widely used and suitable apparatus for the infinite dosing technique of percutaneous absorption are diffusion cells available under the trademark Side-Bi-Side from Crown Glass Company, Inc., 990 Evergreen Drive, Somerville, N.J. 08876. This apparatus employs a pair of horizontally disposed glass diffusion cells having planar ground glass surfaces between which the skin membrane is held in a fluid tight joint and in communication with the interior of both cells. The cells are held together by a combination holding and clamping device. The unsupported area of the skin membrane, i.e., the surface area through which absorption takes place is defined by an orifice in the planar glass surfaces on either side of the membrane. Since the glass diffusion cells must be hand blown because of their configuration, it is inherent that the orifices vary slightly in diameter and roundness and consequently define a somewhat different surface area exposed to the membrane which adversely affects the accuracy of the absorption test results.

An alternative technique is the finite dose technique which utilizes an apparatus known as the Franz cell. Vertically disposed glass vessels are separated by the membrane and communicate through an orifice in each of the cells on either side of the membrane. The donor solution is present in the upper vessel and a receptor solution in the lower vessel. The Franz cell is constructed from blown glass and, like its counterpart used for the infinite dose technique inherently has the problem of slightly differing surface areas in the opposing orifices.

SUMMARY

The improvement of the invention can be used with either the infinite or finite dosing technique. An orifice assembly is provided for holding a porous membrane in a fluid tight relationship between a pair of glass diffusion cells. The orifice assembly includes a first male and second female member each having an outer planar surface for mating in a fluid tight seal with one of said glass diffusion cells, and an inner planar surface adapted to receive and securely retain the porous and flexible membrane in combination with the inner surface of the other member. Each member has a centrally disposed orifice which is co-extensive with the orifice of the corresponding member and has a lesser surface area than the open end of each of the diffusion cells. The orifice assembly is constructed of a resiliant material which is resistant to fluid leaching and absorption of the active ingredient.

A primary advantage of the invention is the exposure of the same precise and predetermined surface area of the membrane to both donor and receptor solutions during percutaneous absorption. A further advantage of the invention is the provision of a combination of mating grooves and projections and related internal and external gasketed areas to insure the consistant physical integrity of the typically fragile membrane and the fluid tight relationship between the orifice assembly and the diffusion cells. Additional advantages are the simple and easily repeatable loading of the membrane into the holder member and the chemical versatility of the orifice member when constructed of the recommended materials.

DRAWINGS

DETAILED DESCRIPTION

Figures 1, 2, 3, 4:
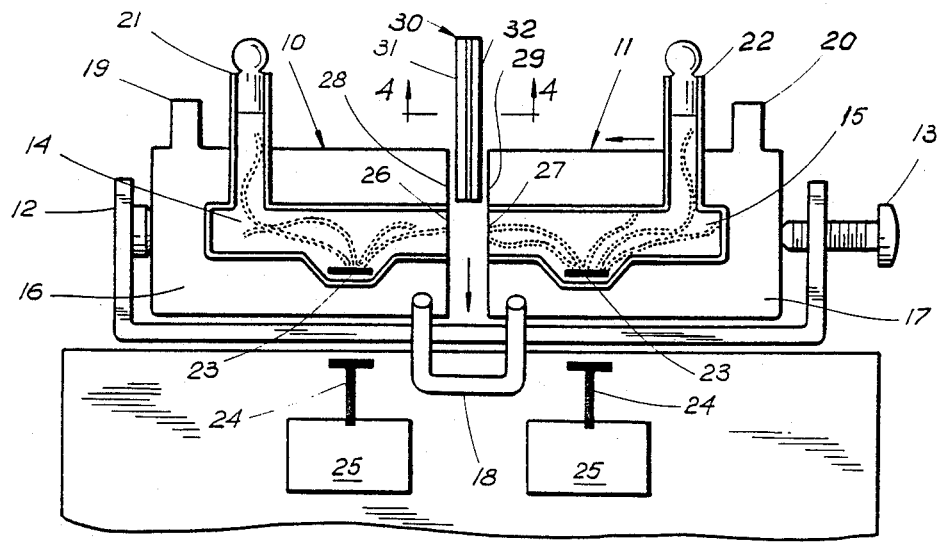
FIG. 1 is a schematic view of an apparatus for the percutaneous absorption of fluids including the improvement of the invention.
FIG. 2 is an exploded view of the orifice assembly of the invention.
FIG. 3 is a cross sectional view of the orifice assembly of the invention.
FIG. 4 is a cross sectional view of the orifice assembly taken along line 4—4 of FIG. 1.

Referring to FIG. 1 a pair of horizontally disposed diffusion cells 10, 11 are shown with a holding device 12 having clamping means 13 for securely joining the cells together. Each cell has a donor reservoir 14 or receptor reservoir 15 and jackets 16, 17 for circulating cooling water under controlled conditions around reservoirs 14, 15 from inlet 19 through connecting tube 18 and outlet 20. The reservoirs 14, 15 and jackets 16, 17 are circular in cross section, are made of glass and because of their configuration must be individually hand blown. The donor reservoir 14 is supplied through conduit 21 with a solution to which an active ingredient such as a pharmaceutical, cosmetic or toxic compound whose rate of absorption through a membrane is to be measured has been added. The receptor reservoir 15 is supplied with the same solution without active ingredient through conduit 22. The solution is agitated in both reservoirs 14 and 15 by magnetic stirrers 23 which are activated by revolving drive magnets 24 and motors 25. After a given time the amount of solute (active ingredient) present in the receptor solution is measured. The result is the percutaneous absorption rate.

The reservoirs 14, 15 each terminate at one end with orifice 26, 27. Each orifice 26, 27 is circular and is defined by the planar surfaces 28, 29 making up the terminus of jackets 16, 17. The diameters of the orifices inevitably differ slightly because the reservoirs and jackets are hand blown. Since the rate of absorption through the membrane from reservoir 14 to reservoir 15 is a function of the surface area and consequently diameter of orifices 26, 27 the inherent difference in diameter between the two contributes to inaccurate results.

Referring to FIGS. 2–4 and in accordance with the invention there is provided an orifice assembly 30 comprising a pair of male and female holder members, 31 and 32 respectively. The holder members 31 and 32 are adapted to securely retain a thin flexible membrane 33 typically human or animal skin, therebetween. Each holder member 31, 32 has a flat planar outer surface 34, 34A and a centrally disposed hole 35, 36. Each hole, 35, 36 has the same area in a plane parallel to the planar outer surface 34, 34A. Although the holes 35, 36 are preferably round they can be any desired shape such as oval. Pursuant to a preferred embodiment of the invention, the holes 35, 36 are circular and have the same diameter. The outer periphery of each of the holder members 31, 32 is provided with an alignment groove 37, 38 that is positioned so that when they align the holes 35, 36 are congruent. To secure the membrane 33 in place between the inner planar surface 40 of male holding member 31 and inner planar surface 41 of female holding member 32 a mating groove 42 and projection 43 is provided adjacent the respective inner planar surfaces 40, 41. The groove 42 and projection 43 are circular, are continuous as shown in FIGS. 2 and 3 and have an angular cross section. Preferably the groove 42 has a sloping surface 44 which forms an obtuse angle 45 with the adjacent inner planar surface 40 and the projection 43 has a corresponding sloping surface 46 which forms the same obtuse angle 45 with the adjacent inner planar surface 41.

In accordance with a specific aspect of the invention the projection 43 comprises an outer peripheral surface 47 which is normal to the inner planar surface 41 and opposite the sloping surface 46. The surface 47 includes a sealing or securing means 48, preferably in the form of an O-ring gasket, which functions to securely fasten together the holding members 31 and 32.

In accordance with a further specific aspect of the invention sealing means 49 is provided on a portion of the planar outer surface 34, 34A of the holding members 31 and 32. The sealing means 49 is preferably a resilient O-ring gasket and functions to form a fluid tight joint between surfaces 34, 34A and the corresponding surfaces 28, 29 of the reservoirs 14, 15.

To further insure proper and consistant alignment of the diffusion cells 10, 11 with the orifice assembly 30 planar outer surfaces 34, 34A are each provided with a peripheral flange 50, 51 which abut around a portion of the circumference of the diffusion cells.

To insure proper usage of the new and improved orifice assembly of the invention, a membrane support plug 52 is employed. The plug 52 has a projecting surface 53 and is adapted to insert into the orifice 36 of female holder member 32 to form a coextensive planar surface with the inner planar surface 41. Shoulder 54 abuts outer surface 34A to provide proper alignment of the surfaces 53 and 41. In practice, the membrane 33 is applied to the coextensive planar surfaces 53 and 41 and the male holder member 31 is joined together with female member 32 as shown in FIG. 3. The plug 52 is removed to form the orifice assembly of FIG. 4 ready for use between the surfaces 28, 29 of the diffusion cells 10, 11.

The orifice assembly 30 is used in connection with the diffusion cell apparatus shown in FIG. 1 by placing the assembly between the planar surfaces 28, 29 and securely clamping it therebetween in fluid tight relationship using the clamping means 13. The identical and aligned holes 35, 36 are slightly smaller in surface area and in the case of round holes, diameter than either of the orifices 26, 27 and are disposed so that a known and predetermined surface area of membrane 33 is exposed to the solution of active ingredient in the donor reservoir 14 and bathing solution in the receptor reservoir 15.

According to the invention the holder members 31, 32 are fabricated from a resiliant material that is resistant to fluid leaching and does not absorb the carrier solution or active ingredient. A suitable material of construction is teflon; alternatives include polyester resins having the required characteristics. Preferably the holder members are fabricated from steel with a coating of teflon or other suitable polymer. The O-ring gaskets may be a fluorocarbon resin for greatest chemical flexibility.

We claim:

1. An orifice assembly comprising first and second holder members, each of said holder members having means defining a centrally disposed orifice, an exterior planar surface including a sealing means, and an annular interior planar surface parallel to each of said respective exterior planar surfaces and adjacent to and concentric with each said respective orifice, said interior planar surfaces being positioned and arranged to receive and retain a flexible membrane therebetween, said interior and exterior planar surface being on opposite sides of each of said first and second holder members, said first holder member having a continuous annular projection disposed adjacent to and concentric with the interior planar surface of said first holder member, said projection extending outwardly from said interior planar surface of said first holder member and including a first outer peripheral surface normal to said exterior planar surface of said first holder member including a gasket means and a first inner sloping surface, said second holder member having a continuous annular groove disposed adjacent to and concentric with the interior planar surface of said second holder member, said groove being recessed from the interior planar surface of said second holder member and including a second outer peripheral surface normal to the exterior planar surface of said second holder member and positioned and arranged to seal against said gasket means and to securely fasten together said first and second holder members and a second inner sloping surface corresponding to said first inner sloping surface, both of said orifice having the same diameter and aligned to be coextensive when said groove and said projection are positioned and arranged in a mating relationship.

* * * * *